US007175587B2

(12) United States Patent
Gordon et al.

(10) Patent No.: US 7,175,587 B2
(45) Date of Patent: Feb. 13, 2007

(54) METHOD AND APPARATUS FOR PULSED ELECTROMAGNETIC THERAPY

(75) Inventors: Glen A. Gordon, Port Gamble, WA (US); Donald C. Haueisen, Olalla, WA (US)

(73) Assignee: EM-Probe, Inc., Port Gamble, WA (US)

( * ) Notice: Subject to any disclaimer, the term of this patent is extended or adjusted under 35 U.S.C. 154(b) by 0 days.

(21) Appl. No.: 10/749,324

(22) Filed: Dec. 31, 2003

(65) Prior Publication Data

US 2004/0230224 A1 Nov. 18, 2004

Related U.S. Application Data

(60) Provisional application No. 60/437,247, filed on Dec. 31, 2002.

(51) Int. Cl.
*A61N 2/00* (2006.01)
(52) U.S. Cl. .......................................................... 600/9
(58) Field of Classification Search ............... 600/9–15
See application file for complete search history.

(56) References Cited

U.S. PATENT DOCUMENTS

| 4,674,482 A | 6/1987 | Waltonen et al. |
| 4,982,742 A | 1/1991 | Claude |
| 5,058,582 A | 10/1991 | Thaler |
| 5,088,976 A | 2/1992 | Liboff et al. |
| 5,195,941 A | 3/1993 | Erickson et al. |
| 5,269,747 A | 12/1993 | Erickson et al. |
| 5,314,401 A | 5/1994 | Tepper |
| 5,338,286 A | 8/1994 | Abbott et al. |
| 5,351,389 A | 10/1994 | Erickson et al. |
| 5,370,680 A | 12/1994 | Proctor |
| 5,478,303 A | 12/1995 | Foley-Nolan et al. |
| 5,518,496 A | 5/1996 | McLeod et al. |

(Continued)

FOREIGN PATENT DOCUMENTS

DE 103 52 000 A1 6/2005

(Continued)

OTHER PUBLICATIONS

Declaration of Glen A. Gordon, M.D., dated Dec. 23, 2005, and Attached Exhibits A-C.

(Continued)

*Primary Examiner*—John P. Lacyk
(74) *Attorney, Agent, or Firm*—Klarquist Sparkman, LLP (57) ABSTRACT

An apparatus and method for applying pulsed electromagnetic therapy to humans and animals. A straight wire element is employed to generate the magnetic field. A power and timer circuit supplies current pulses that approximate square pulses in form, so that the straight wire element generates magnetic pulses having rapid rise and fall times. Peak field strength is approximately 2 gauss at a 1 cm distance from the straight wire element, and the duration of peak field strength is approximately 200 nanoseconds. The pulses are repeated at a frequency of about 70 Hz. The straight wire element and circuit may be housed in a hand-held probe, with an LED illuminating the skin area to provide a visual indication of effective range, or a plurality of the straight wire elements and associated circuits may be embedded in a conformable pad that is placed over the affected area of the body.

20 Claims, 5 Drawing Sheets

U.S. PATENT DOCUMENTS

| | | | |
|---|---|---|---|
| 5,743,844 | A | 4/1998 | Tepper et al. |
| 6,132,362 | A | 10/2000 | Tepper et al. |
| 6,234,953 | B1 | 5/2001 | Thomas et al. |
| 6,261,221 | B1 | 7/2001 | Tepper et al. |
| 6,418,345 | B1 | 7/2002 | Tepper et al. |
| 6,443,883 | B1 | 9/2002 | Ostrow et al. |
| 6,463,336 | B1 | 10/2002 | Mawhinney |
| 6,485,963 | B1 | 11/2002 | Wolf et al. |
| 6,561,968 | B1 | 5/2003 | Dissing et al. |

FOREIGN PATENT DOCUMENTS

| | | |
|---|---|---|
| WO | WO 94/01176 | 1/1994 |
| WO | WO 2005/001496 | 1/2005 |

OTHER PUBLICATIONS

"Introduction," 4 pp. (document marked May 5, 2005, May 10, 2005, and Dec. 28, 2005) (downloaded from http://www.papimi.gr/introduc.htm on Jun. 21, 2006).

Jorgensen et al., "Electrochemical Therapy of Pelvic Pain: Effects of PEMF on Tissue Trauma," 11 pp. (document marked as being published in 1994) (downloaded from http://www.papimi.gr/report01.htm on Jun. 23, 2006).

"PAPIMI Device and PAPIMI Treatments," 9 pp. (document marked as updated Sep. 7, 2002) (downloaded from http://www.papimi.gr/products.htm on Jun. 21, 2006).

"Pulsed E/M Energy Devices Summary," 1 p. (document undated) (downloaded from http:www.papimi.gr/compar.htm on Jun. 21, 2006).

"Short Description of PAP IMI Device," 5 pp. (document marked May 1, 2005) (downloaded from http://www.papimi.gr/compar.htm on Jun. 21, 2006).

"Welcome to PAPIMI," 8 pp. (document undated) (downloaded from http://www.papimi.gr/index.htm on Jun. 21, 2006).

FIG. 4

METHOD AND APPARATUS FOR PULSED ELECTROMAGNETIC THERAPY

This Non-Provisional patent application claims the benefit of prior Provisional Application Ser. No. 60/437,247, which was filed 31 Dec. 2002.

BACKGROUND OF THE INVENTION a. Field of the Invention

The present invention relates generally to devices for therapeutic application of magnetic fields, and, more particularly, to a compact, portable device for therapeutic application of weak, pulsed electromagnetic fields for human and animal applications.

b. Related Art and Discussion

The therapeutic value of pulsed electromagnetic fields has gained acceptance through the course of studies and clinical applications. Magnetic fluxes are known to penetrate deeply into human tissue with little attenuation, and have been observed to promote both bone and tissue regeneration. Although the physiological mechanism involved is not fully understood and is the subject of competing hypotheses, it is theorized that magnetic field exposures exert the observed effects through induction of electrical currents in the tissues. Moreover, it is believed that these effects occur on a molecular or cellular level.

A number of systems and devices have been developed to apply the observed benefits of pulsed electromagnetic fields in a therapeutic environment. Many or most of these devices have been directed to the promotion of bone growth, specifically the therapeutic treatment of bone fractures. While mostly successful for their intended purpose, difficulty in the use and application of these devices has limited their benefits in the treatment of surrounding soft tissues (e.g., muscles and tendons). field, although a few devices have been developed that use somewhat weaker fields. These devices also employ a comparatively long ramp up to full pulse strength. As a group, these devices have been ungainly and difficult to apply, especially outside a clinical setting, and consequently have limited utility in treatment of soft tissue traumas.

In the course of extended clinical observations, Applicant has found that low-strength, pulsed electromagnetic fields (i.e., fields having a strength more on the order of the naturally occurring magnetic field of the earth) produce results superior to high-strength magnetic fields when applied to soft tissue trauma. Moreover, Applicant has found improved results may be achieved by employing pulses of very brief duration (200 nanoseconds). Examples of such soft tissue trauma include muscle and tendon strain, as well as the more serious traumas associated with fractures and wounds.

Commensurate with these observations, Applicant has developed the nonbonding hypothesis that brief duration pulses and short ramp times (i.e., the time between 0 and maximum magnetic flux) may enhance molecular orientation or other molecular activity in the affected tissues, thereby promoting more rapid healing. In accordance with this hypothesis, one possible mechanism of the increased healing rates may be as follows. Trauma results in oxidative stress, and healing is promoted by neutralizing the oxidant species at the trauma site. Oxidant species are neutralized by naturally occurring antioxidants in the body, however the rate of oxidant species neutralization is greatly increased by using a pulsed electromagnetic field (PEMF) as a momentary homogenous catalyst which aligns reactive (charged) surfaces across flux lines in the PEMF. Through observation and clinical study, Applicant has noted that the more quickly the magnetic field is introduced to and then, after creating its effect, removed from the injured living system, the greater the efficiency of interaction, resulting in increased reaction rates, faster neutralization, and a corresponding faster rate of healing. Give the picosecond nature of chemical reactions, the short, nanosecond catalyst may be advantageous in that it is removed from the tissue before causing an overall slowing of the molecular activity that would outweigh its organizational advantages. Longer, millisecond pulses, by contrast, may create a net slowdown. Moreover, it is hypothesized that the effect of the low-strength magnetic field is superior to the commonly applied high strength fields due to the fact that the low-strength field is not dramatically dissimilar from that in which living systems developed and which all organisms are adapted, i.e., the magnetic field of the earth itself.

Consequently, while the pulsed electromagnetic devices found in the prior art emit sine wave-configured field pulses with relatively slow ramp times, it is Applicant's assertion that pulses of short duration with short ramp times and lower field strengths result in significantly improved injury recovery rates.

As was noted above, prior PEMF therapy devices have also been so large and costly as to be unsuitable for much therapeutic applications, let alone individual use. For example, many are heavy (e.g., several hundred pounds), stationary devices which often surround an entire limb or body of the patient. The large physical size, as well as the broad PEMF footprint, limits their therapeutic application in discrete, less accessible anatomical locations where isolated treatment may be desired. In at least some instances, the size of these devices is driven by the magnetic coil technology that is used, coupled with the perceived need to propagate exceedingly strong magnetic fields. In any event, such devices wholly unsuitable for home use; the benefits are therefore limited to infrequent clinical visits, rather than daily or hourly application, except in the case of hospitalized patients.

Accordingly, there exists a need for a device for pulsed electromagnetic field therapy of soft tissue trauma that propagates a comparatively low strength magnetic field capable of penetrating to muscles, tendons and like tissues. Furthermore, there exists a need for such an apparatus that generates such fields with a comparatively short pulse duration and short pulse ramp times. Still further, there exists a need for such an apparatus that is sufficient inexpensive, portable, and suitable for home use on a frequent or as-needed basis, and which allows treatment in discrete anatomical locations as desired.

SUMMARY OF THE INVENTION

The present invention has solved the problems cited above, and is a method and apparatus for therapeutic application of weak, rapidly induced, pulsed electromagnetic fields for human and animal applications.

Broadly, the method of the present invention comprises inducing into a biological system a pulsed magnetic field, with the pulsed magnetic field having a rapid rise time and a peak magnitude on the order of the earth's magnetic field, for therapeutic treatment of injury, illness, and/or aging. The method may further comprise introducing the pulsed magnetic field with a waveform which approximates a step function, characterized by a rapid, near vertical rise time to peak field strength, followed by a sustained peak field strength for approximately 200 nanoseconds, followed by a rapid, near vertical decay of field strength to approximately zero magnitude. The method may further comprise repeating the pulsed magnetic field with a frequency in the range of about 10–100 hertz.

The apparatus of the present invention may comprise a pulsed electromagnetic field (PEMF) device having at least one electrical circuit for generating a pulsed magnetic field having a rapid rise time and a peak magnetic flux amplitude of the same order as the earth's magnetic field. The circuit may comprise an electrical timing element for driving the magnetic flux according to the prescribed waveform as characterized above for an electrical power source providing the power necessary to generate the magnetic flux and to operate the timing element and sensory indicator.

The apparatus may further comprise a sensory indicator that demarcates the approximate region over which the magnetic flux is generated, allowing the user to focus the magnetic field on the biologically active treatment location.

According to Applicant's non-binding hypothesis, as stated in the foregoing Background section, the short pulse duration accompanied by short ramp times is one factor that contributes to the enhanced therapeutic efficiency of the present invention. This effect is partially achieved by virtue of a lower peak magnetic flux being generated in the invention as compared to the much larger fields introduced by other PEMF devices (it will be understood that the term "straight wire element" is used in this description and the appended claims to distinguish from coils, but that the wire element may not be physically straight per se). In the preferred embodiment, the peak magnetic flux generated may be approximately 2 gauss, on the same order as the earth's field, while typical existing PEMF devices develop field strength orders of magnitude higher. Because these other PEMF devices operate according to an alternative hypothesis which prescribes a much larger field strength, they are incapable of achieving the rapid pulse introduction which Applicant has observed to provide enhanced therapeutic benefit.

Additional contributing factors which allow the present invention to achieve rapid, near vertical rise and fall times are presented through the inherent design of the electrical circuit of which the present PEMP device is comprised. In the preferred embodiment, the electrical components comprising the electrical circuit and timing element may be minimized in terms of size, spatial layout, and quantity. The electrical circuit may be minimally designed to perform only two required functions; to generate a magnetic field pulse according to the method of the invention stated above and power the sensory indicator. By limiting the number of components to those which are absolutely essential for performing these required functions and optimizing the physical layout of the components, the parasitic effects can be minimized allowing the rapid rise and fall times of the magnetic field pulse.

In addition, previous PEMF devices generally use auxiliary, multiple loop transducer coils in order to achieve higher magnetic field strengths, and usually these coils are quite large in order to cover an extensive anatomical treatment site. Consequently, these previous devices are constrained to ramp slowly in developing a peak magnetic flux state. In contrast, the present invention is capable of generating its required magnetic field strength over relatively short time periods due to its inherent design and compact size. In essence, the circuitry required for generating the waveform acts as an intrinsic electromagnetic transducer coil without supplemental coil wiring. Due to this design characteristic and the compact nature of the circuit, the present invention can achieve desirable flux ramp rates which are orders of magnitude faster than those found in the prior art, i.e., nanoseconds versus milliseconds. The magnetic field is generated by a single straight wire element that constitutes a very small inductance compared to the magnetic field coils of most previous PEMF devices. Due to this design characteristic, the present invention can achieve desirable flux ramp rates which are orders of magnitude faster than those found in the prior art, i.e. nanoseconds versus milliseconds.

Aside from the cited performance advantages, additional benefits are achieved through the simplification and miniaturization permitted by strategically limiting the PEMF circuitry requirements to the essential functions. First, the invention may be economically produced and packaged as a lightweight, compact, handheld unit suitable for individual home use. In the preferred embodiment, the electronics may be encased in a compact, inexpensive housing that serves as a low-profile handheld probe. Treatment may accordingly be self administered by passing the probe over the treatment area in a stroking manner for a prescribed duration. Additional treatments may be subsequently repeated as required/desired according to the user's preference and agenda. This is a great advantage in terms of convenience and cost since the patient is not required to schedule clinical visitations or attend clinical facilities.

A second advantage derived from the compact, handheld probe configuration, is the ability to focus the treatment exclusively on the injury site regardless of its anatomical location. Many of the existing PEMF devices are designed to be site specific. Consequently, they are anatomically configured to treat a specific body part which precludes their use at other locations and severely limits their utility. Many other existing PEMF devices are large, cumbersome affairs or stationary units designed to treat entire portions of the body regardless of the bodily extent of the trauma. While the exposure of healthy tissue to magnetic treatment is not necessarily injurious, such treatment is unwarranted. Furthermore, the ungainly bulk and mass of these units often inhibits their ability to treat locations which are not readily accessible. In contrast, due to its light weight and slim profile, the present invention may be easily manipulated to access and treat discrete locations on virtually any portion of the body. Moreover, the treatment is highly localized, eliminating the unwarranted treatment of healthy tissue according to the user's discretion.

When configured as a handheld probe, the invention may be equipped with a sensory indicator that demarcates the approximate region over which the magnetic flux is generated. Although not essential for operation, the implementation of a field indicator is advocated due to the decay of electromagnetic field strength over distance combined with the low field strength being induced. The indicator may be a visual signal, such as focused illumination from an LED, a tactile indicator, or of some other form. Regardless of format, the indicator should provide the user with feedback as to whether the magnetic field is appropriately permeating the trauma site, thus confirming that proper treatment is being received.

In another embodiment, the invention may be reconfigured to provide broader magnetic coverage for convenient treatment of larger trauma regions or regions of specific anatomical shape. By using multiple PEMF circuits, each comprising its own field generation and timing circuit, a patterned network of replicated devices may be interconnected to form a surface array. Using appropriate control circuitry, the individual PEMF circuits may be sequentially or simultaneously activated in a cyclic manner to generate the required pulsed waveform, and each PEMF circuit may accordingly provide magnetic field effects in the designated region that it occupies within the array. The collective field effect footprint may be controlled by the spacing and geometric arrangement of the individual PEMF devices within the array, allowing the coverage area to be configured in a variety of shapes and sizes.

The compilation of PEMF circuits may then be packaged in a variety of ways according to the intended application. For example, they may be packaged in a larger version of the handheld probe previously discussed, thus reducing the translational stroking motion required to treat larger trauma sites. Or, as another example, the circuits may be embedded in a conformal pad, which envelopes the trauma site and conforms to the site's anatomical contours by gravity, securement straps, or applied pressure. By such embodiments, the invention may achieve extensive treatment site coverage and/or site-specific coverage like other PEMF devices. Yet, while other PEMF devices are handicapped by their slow magnetic response, the present invention can produce the pulses and quick ramp times that account for its enhanced therapeutic efficiency.

The invention, together with further aspects and advantages thereof, will be further understood by reference to the following detailed description and accompanying drawings.

DETAILED DESCRIPTION a. Overview

Figure 1:
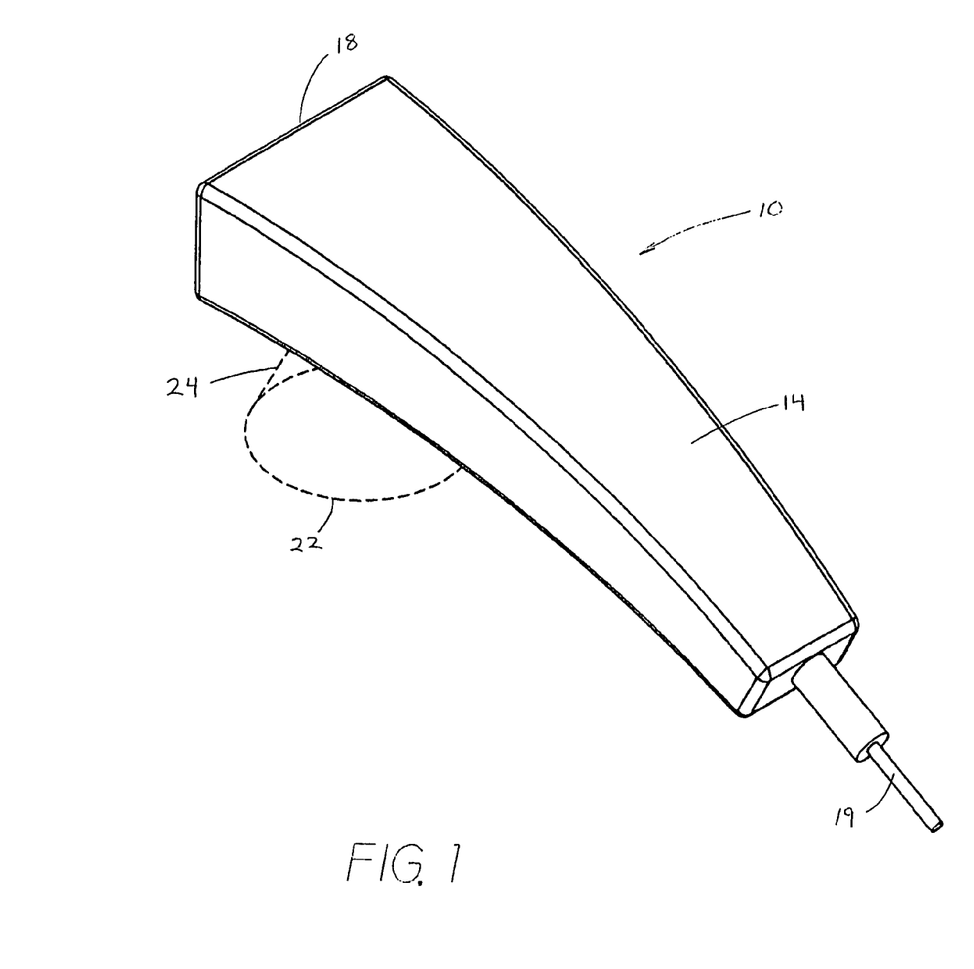
FIG. 1 is a perspective view of a handheld probe for therapeutic application of a pulsed magnetic field in accordance with the present invention.
Figure 2:
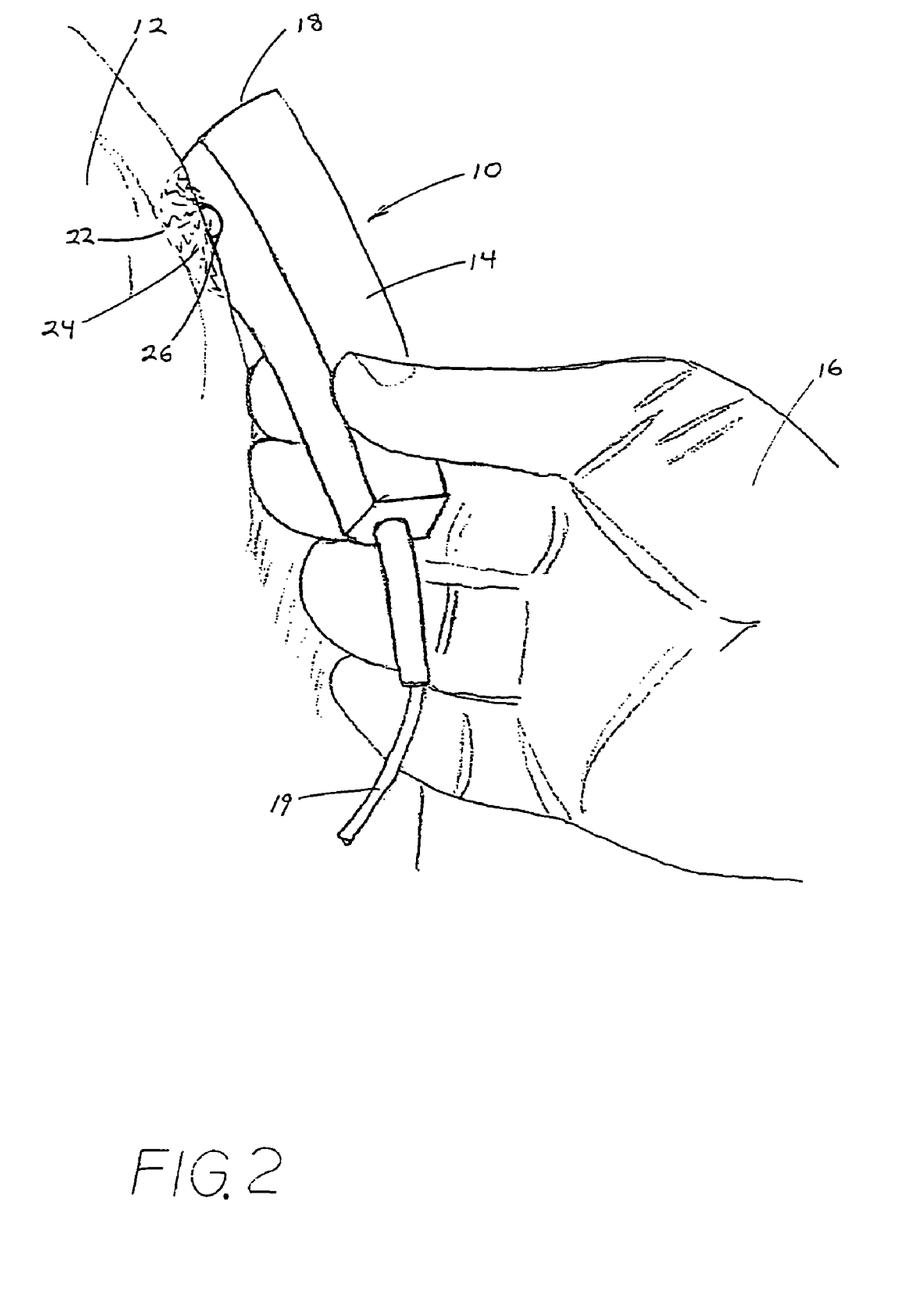
FIG. 2 is a perspective view of the handheld probe of FIG. 1, showing the probe being used to treat an example trauma site adjoining the knee of a patient.

FIG. 1 provides an isometric overview of a PEMF therapy probe 10 in accordance with a preferred embodiment of the present invention, while FIG. 2 shows the probe being used to treat the knee 12 of a patient. In this preferred embodiment, the device 10 includes a lightweight, compact housing 14 which is easily gripped in the hand 16 of the user for self-application. The housing 14 encloses the functional electronics of the device and may be molded from plastic or fabricated from other suitable materials. In the preferred embodiment, the housing 14 is a commercially available molding made from polymeric material, which helps reduce costs. The functional electronics, including the straight wire element that generates the magnetic field, are integrated on a circuit board (not shown) that is mounted and enclosed within the housing 14 proximate the distal end 18 thereof. Power is supplied to the circuit via transformer by a power cord 19 which is plugged into a standard 120 volt AC household receptacle. An LED 20 (see FIG. 4), mounted on the circuit board, serves as a sensory indicator which illuminates the effective treatment zone 22 by projecting a beam of light 24 through an aperture 26 in the housing 14. Using the illuminated treatment zone 22 as a guide, the user then passes the probe over the trauma site in a stroking manner for approximately 30 minutes. Alternatively, it may simply be placed against the affected area under a light restraint (e.g., under a lightweight glove when treating carpal tunnel syndrome, or under a T-shirt when treating a sore back muscle), where it will remain in place due to the low weight of the probe relative to its area of contact against the skin. Reapplication of the therapy treatment may be repeated according to the user's requirements and schedule.

b. Method

As previously discussed, the goal of the device is to promote healing by generating a pulsed electromagnetic field. As substantiated through clinical observations by Applicant, this is achieved most efficiently using short duration pulses, short ramp times, and a peak magnetic flux magnitude comparable in strength to the earth's magnetic field.

Figure 3:
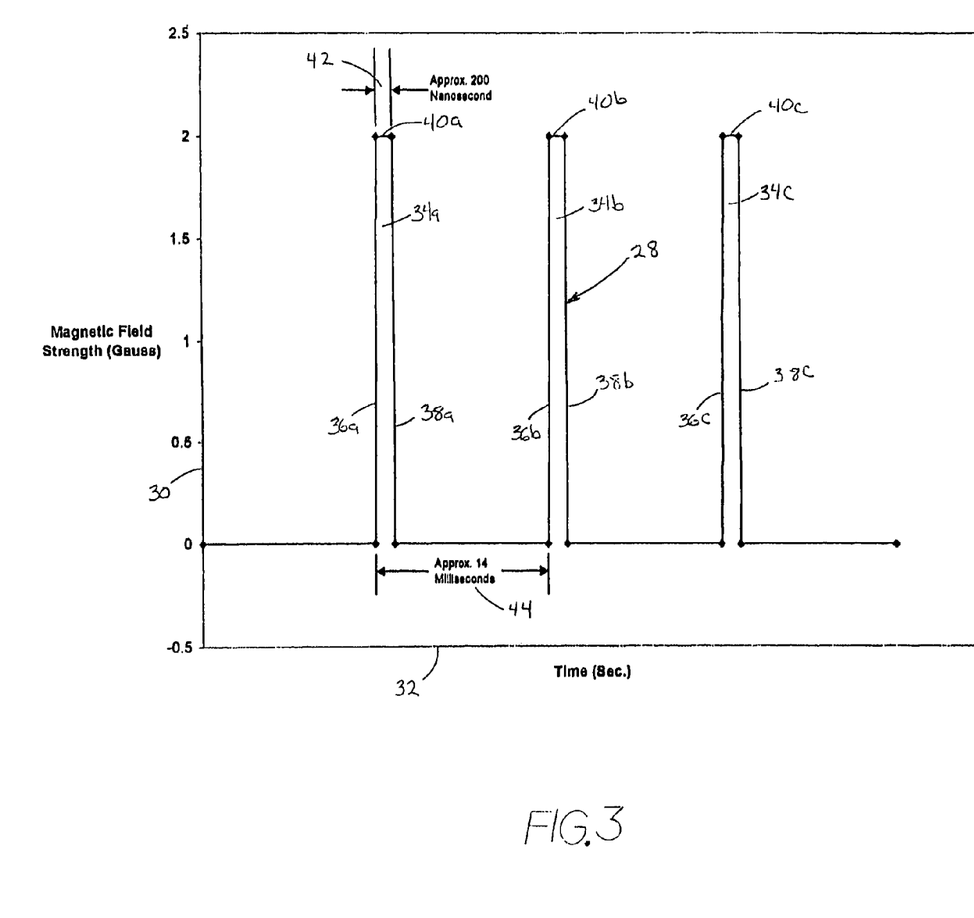
FIG. 3 is graphical view showing the preferred magnetic waveform generated by the handheld probe of FIG. 1.

A desirable field pulse 28 for achieving this goal is produced by the circuitry exemplified in the preferred embodiment, and is shown in the graph constituting FIG. 3. FIG. 3 shows the magnetic output magnitude of the probe 10 using the Y-axis 30 to represent flux amplitude and the X-axis 32 to represent time. In order to illustrate the shape of the waveform peaks 34a–c, it is necessary to exaggerate the time between the rise 36a–c and corresponding decay 38a–c portions of the curve. Consequently, the graph is provided for illustrative purposes only, and for clarity the time scale of the waveform 28 is deliberately displayed without proportional accuracy.

As illustrated, the peak magnetic flux amplitude 40a–c in the preferred embodiment is low-level, generally less than 3–5 gauss and preferably approximately 2 gauss at 1-centimeter distance. This is the same order of magnitude as the earth's magnetic field (approximately 0.5 gauss) in which all organisms are adapted, and, according to Applicant's hypothesis, provides superior healing rates compared to the high levels promoted by other PEMF devices.

The waveform 28 approximates a square pulse with rapid rise and fall times 36a–c to peak and near vertical decay times 38a–c to zero. The rapid introduction of the peak flux complies with the observation that the faster the flux is introduced to the injured living system, the greater the efficiency of interaction resulting in increased reaction rates and faster neutralization. As illustrated by the dimensioned extension lines 42 on the first peak 34a, the sustained peak amplitude is very short, generally less than about 300 nanoseconds and preferably approximately 200 nanoseconds. This rapid pulse is critical for achieving a more effective response in the biological system, without (it is believed) causing a counterproductive slowing of overall reactivity, as may develop when using longer durations pulses. In contrast, most other PEMF devices utilize slowly ramping fields and/or lower frequency pulses which peak at levels orders of magnitude higher than in the present invention.

The time lapse between consecutive peaks in this example is approximately 14 milliseconds, as indicated by the dimensioned extension lines 44. This value is orders of magnitude larger than the sustained peak value (200 nanoseconds) 42, and is consequentially derived from the pulse frequencies which Applicant has observed to provide enhanced therapeutic benefit. The preferred frequencies lie in a range from about 10 to 100 hertz. However, Applicant has discovered through empirical study that approximately 70 hertz is optimal, possibly due to induced resonances. The preferred embodiment therefore utilizes a frequency of approximately 70 hertz which results in the 14 millisecond lapse time.

In addition to providing specific details on the exemplary embodiment of the method of the invention, the method has been described in general terms by providing preferred ranges for waveform characteristics such as frequency and amplitude. These descriptions are intended for illustrative purposes, and are not meant to be restrictive. It is understood that alternative embodiments, as well as modifications in pulse shape and characteristic values, will be suggested to those skilled in the art. It is further understood, that this invention encompasses any modifications or alternative methods that fall within the scope of the appended claims.

c. Circuit Design

Figure 4:
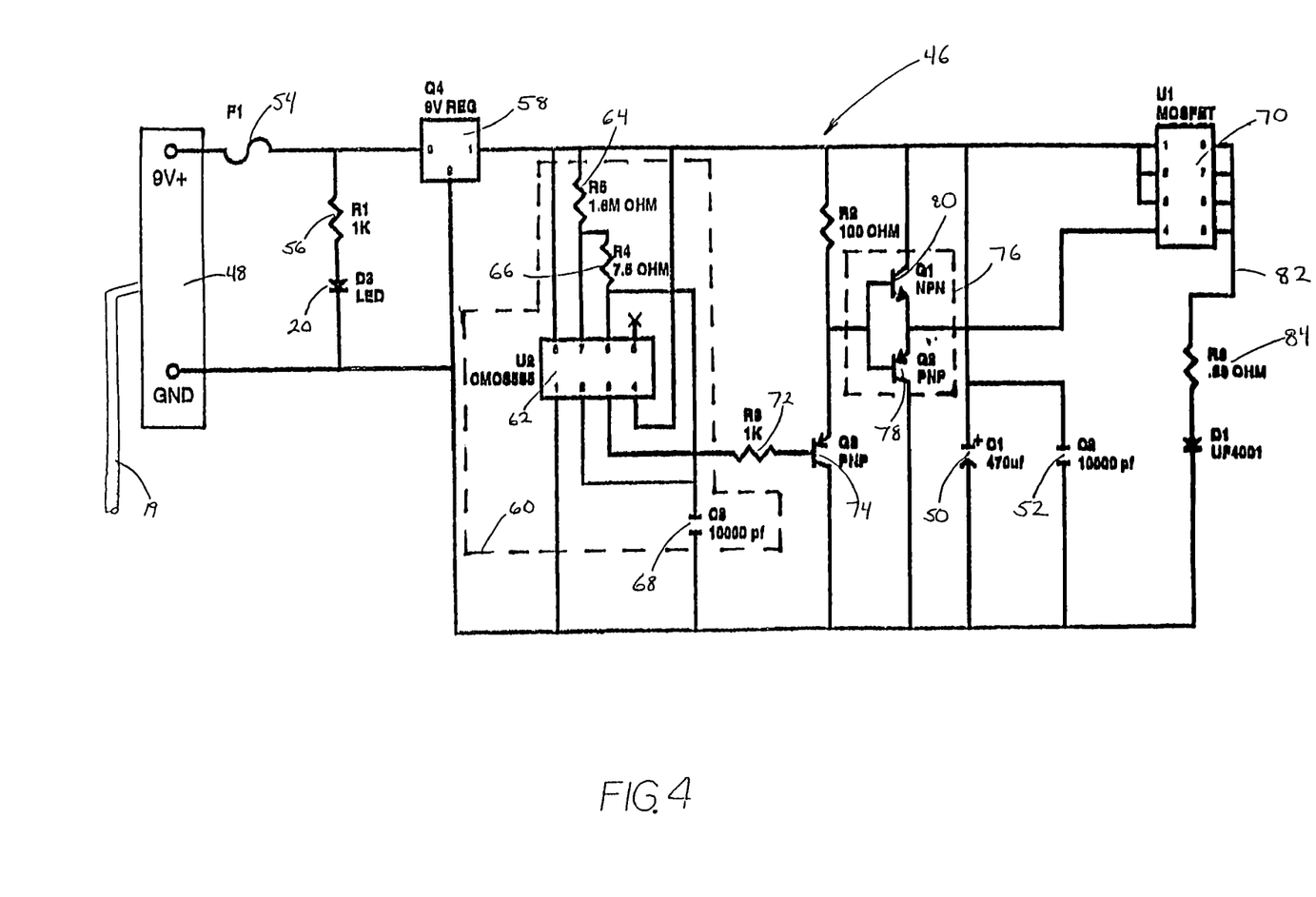
FIG. 4 is a diagrammatic view showing the flux generation and pulse timing circuit of the therapeutic probe of FIG. 1.

To generate the prescribed waveform 28, the preferred embodiment uses an integrated flux generation and timing circuit 46 which is illustrated in the circuit diagram constituting FIG. 4. The various circuit elements comprising the circuit are commercially available components as tabulated below:

The circuit elements enclosed by the dotted line 60 constitute a monostable multi-vibrator or oscillator, and include a CMOS555 timer 62, a 1.5 mega-ohm resistor 64, a 7.5-ohm resistor 66, and a 10,000 Pico farad capacitor 68. In the preferred embodiment, the multi-vibrator 60 is essentially a switching unit which sets the pulse width and repetition rate in accordance with the electromagnetic pulse requirements as specified in the foregoing Method section. The CMOS555 timer 62 is the heart of the unit and is intended for high speed switching of relatively low current circuitry. Consequently, the multi-vibrator 60 is incapable of directly toggling the 15–20 amp current which is required to generate the 2 gauss magnetic field in the circuit. Accordingly, the multi-vibrator 60 serves as a preliminary switching element in a low current sub-circuit whose output is subsequently amplified and used to trigger a MOSFET 70 that acts as the main circuit power switch.

Output from the multi-vibrator 60 is amplified in two stages. The first stage is a PNP follower circuit 74, and the second is a push-pull driver circuit 78, 80, indicated by the dotted line 76. The push-pull drives the gate of the MOSFET 70. The push-pull driver circuit 76 comprises a second PNP transistor 78 and a 40 volt, 100 milliamp NPN transistor 80.

The MOSFET 70 has low inductance, low resistance and a fast transient response time. Thus when the amplified

| Part Description | QNTY | REF# | SMT PKG | MFG | MFG# |
|---|---|---|---|---|---|
| Transformer, 9 VDC 500 mA, 2.1 mm | 1 | | | CUI Inc. | DPD090050-P5P-ND |
| CONN, 2.1 mm Panel Mnt Jack | 1 | X1+, X2gnd | | CUI Inc. | PJ-005A |
| 9 V, 100 ma, Pos. Volt Reg | 1 | Q4 | SOT-89 | NJR | NJM78L09UA |
| CMOS 555 Timer | 1 | U2 | SO-8 | NATIONAL | LMC555CM |
| NPN Transistor, ssgp 40 V, 100 mA | 1 | Q1 | SOT-323 | DIODES IN | MMST3904-7 |
| PNP Transistor, ssgp 40 V, 100 mA | 2 | Q2, Q3 | SOT-323 | DIODES IN | MMST3906-7 |
| MOSFET, Single P-CH −30 V | 1 | U1 | SO-8 | FAIRCHILD | NDS94435A |
| DIODE, UF4001 | 1 | D1 | DO-41 | FAIRCHILD | UF4001 |
| LED | 1 | D3 | 1206 | STANLEY | |
| RES, .39 ohm 5% ½ W | 1 | R6 | 2010 | PANASONIC | ERJ-12ZZQJR39U |
| RES, 100 ohm 5% ¼ W | 1 | R2 | 1210 | PANASONIC | ERJ-14YJ101U |
| RES, 1K 5% ¼ W | 2 | R1, R3 | 1210 | PANASONIC | ERJ-14YJ102 |
| RES, 1.5 M 5% ¼ W | 1 | R5 | 1210 | PANASONIC | ERJ-14YJ155U |
| RES, 7.5 ohm 5% ¼ W | 1 | R4 | 1210 | PANASONIC | ERJ-8GEYJ7R5V |
| CAP, 470 uf 25 V ELECT FK | 1 | C1 | | PANASONIC | EEV-FK1E471P |
| CAP, 10000 pf 50 V Ceramic X7R | 2 | C2, C3 | 1206 | TAGEO | 1206R103K9B20D |
| Fuse, Polyswitch .14 A Reset | 1 | F1 | | RAYCHEM | MINISMDC014-2 |

In the preferred embodiment, the circuit receives power from a cord 19 that plugs into a standard 120 volt AC household receptacle, via a 9-volt DC transformer/rectifier 48, voltage regulator 58, and filter capacitors. The average circuit current used to generate the 20 A pulsed output and 2 gauss magnetic field is less than 1 mA due to the very low duty cycle. Storage capacitors 50, 52 maintain an approximate 9V supply during the pulse discharge. To prevent the risk of electrical injury a 140 mA polyswitch reset fuse 54 is inserted into the positive power lead from the transformer. Although in the preferred embodiment power is delivered to the circuit via a 120 VAC source, the device may alternatively operate from a 9V battery or an automotive 12V circuit.

The LED 20, is driven from the unregulated DC supply, and serves as the sensory indicator by providing a focused illumination of light which roughly corresponds with the footprint of the induced magnetic flux. A 1000-ohm resistor 56 limits current to the LED 20 to prevent overloading.

signal from the multi-vibrator triggers the MOSFET 70, the current in the output circuit rises rapidly generating the rapidly rising magnetic field pulse. However, as previously mentioned, without modulation the current delivered to the primary circuit 82 by the transformer 48 is less than the 15–20 amps required to develop the desired magnetic flux. This is resolved by supplementing the transformer current with current released from built up charge stored in two capacitors 50, 52. The larger capacitor 50 is a 470-microfarad capacitor which provides the bulk of the supplemental current, but delivers it at a slower rate. The smaller capacitor 52, necessitated by the comparatively slow response of the larger capacitor 50, is a 10000 pico-farad capacitor which delivers less current, but at a much faster rate. The small capacitor 52 thus compensates for the slow transient response of the large capacitor 50 by providing the rapid initial ramp up current, which this is subsequently augmented by the larger charge in capacitor 50. Working in conjunction with one another, the two capacitors deliver the required current amplitude at a rate which is compatible with the magnetic field waveform dictated by the method of the present invention. A 0.39-ohm resistor 84, in the primary circuit loop 82, limits the current to the required 15–20 amp level.

Although the preferred embodiment of the circuit as described provides performance characteristics in accordance with the exemplary embodiment of the method of the invention, it is understood that alternative electrical components and circuit configurations may be utilized to achieve the same desirable waveform characteristics as described. Furthermore, it is understood that waveforms variation may be utilized which remain in accordance with the essence of the method of the invention, and that those skilled in the art, will accommodate such variations by employing alternative circuit configurations.

d. Alternative Embodiments

Figure 5:
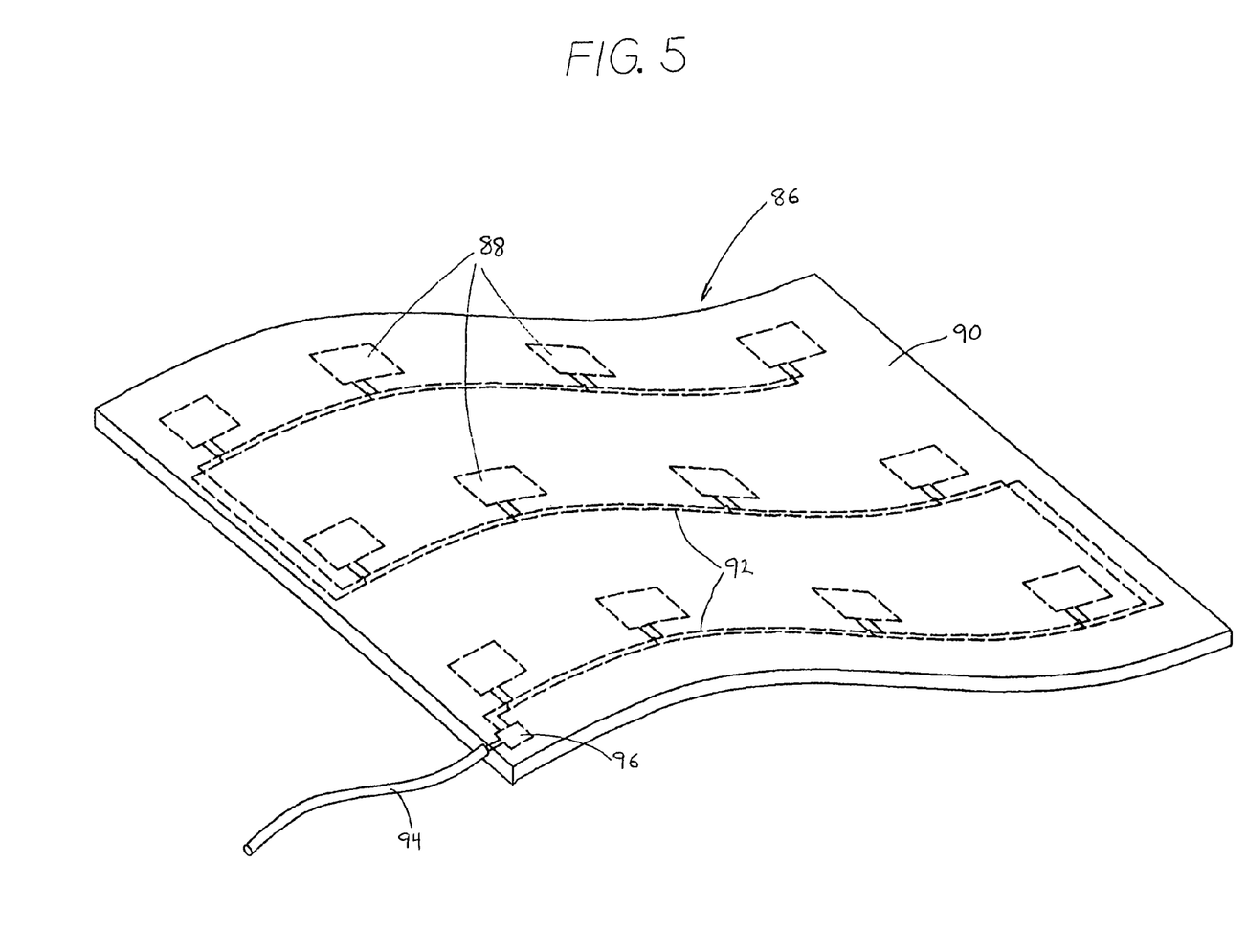
FIG. 5 is a perspective view of a therapeutic pad in accordance with another embodiment of the present invention, having a plurality of PEMF circuits for generating magnetic pulses over an area of the user's body when lying stationary against the skin rather than being moved about in the manner of the probe of FIG. 1.

As an alternative to the single PEMF circuit probe design of the preferred embodiment described above, the invention may be configured to provide broader magnetic coverage for convenient treatment of larger trauma zones or regions of specific anatomical shape. Referring to FIG. 5, such an alternative embodiment 86 is illustrated in which a plurality of interconnected PEMF circuits 88 is embedded in a conformal pad 90.

The PEMF circuits 88 are identically replicated and arranged as a rectangular array within the pad 90, with each PEMF circuit comprising an integrated flux generation and timing circuit 46 as described for the preferred embodiment 10 and shown in the circuit diagram of FIG. 4. The individual PEMF circuits 88 are electrically interconnected by wiring 92 configured to provide simultaneous pulsed operation of the individual PEMF circuits. The power required for operation is relayed through a 120 volt AC power cord 94 and appropriately amplified, according to the power requirements of the array, using amplification circuitry 96.

The pad 90 may comprise a pliable polymeric material, such as latex, silicone, or polyurethane rubber, which is integrally molded around the various electrical components as a flat, flexible sheet. The sheet 90 may be made to conform to the anatomical contours of the trauma site by various means such as gravity, securement straps, or applied pressure. By appropriately positioning the individual PEMF circuits 88 within the pad 90, the magnetic overlap between adjacent PEMF circuits can be sufficiently allocated to eliminate interruption of the magnetic field. Consequently, the peripheral shape of the pad 90 determines the effective footprint of the induced magnetic treatment.

As warranted, the number and positioning of the PEMF circuits 88 within the array, as well as the peripheral shape of the array itself, may be alternatively configured according to the intended application. For example, a larger or smaller PEMF pad 86 could be configured using additional or fewer PEMF circuits 88 to respectively treat larger or smaller trauma sites. Or, for example, by positioning the PEMF circuits to acquire an array with a particular peripheral shape, the pad may conform to a specific body part.

It is noted that various themes of the alternative embodiment may be utilized which capture and remain in accordance with the spirit of the invention as exemplified in the foregoing description. For example, the pad 90 may be constructed from a variety of homogeneous or laminated materials that provide a conformal envelope for the PEMF array. As another example, the PEMF circuits 88 may be electronically configured to provide sequential or patterned pulses as opposed to the simultaneous field pulse previously described.

It is to be recognized that various alterations, modifications, and/or additions may be introduced into the construction and arrangement of parts described above without departing from the spirit or ambit of the present invention as defined by the appended claims.

What is claimed is:

1. An apparatus for applying pulsed electromagnetic therapy to humans and animals, said apparatus comprising:
   a straight-wire element for generating a magnetic field in response to flow of a current pulse therethrough;
   a circuit for supplying to said straight wire element a current pulse that approximates a square pulse in form, so that said straight-wire element generates a magnetic pulse having rapid rise and fall times; and
   a portable housing containing said circuit and straight-wire element so that said straight wire element can be placed in close proximity with an affected area of a body.

2. The apparatus of claim 1, wherein said straight wire element is formed integrally with said circuit.

3. The apparatus of claim 1, wherein said magnetic pulse generated by said straight wire element has a sustained peak field strength duration of less than about 300 nanoseconds.

4. The apparatus of claim 3, wherein said magnetic pulse has a duration of about 200 nanoseconds.

5. The apparatus of claim 3, wherein said magnetic pulse has a peak field strength of less than about 3–5 gauss at a 1 cm distance from said straight wire element.

6. The apparatus of claim 5, wherein said magnetic pulse has a peak field strength of about 2 gauss at a 1 cm distance from said straight wire element.

7. The apparatus of claim 5, wherein said magnetic pulse is repeated with a frequency in the range of about 10–100 Hz.

8. The apparatus of claim 7, wherein said magnetic pulse is repeated with a frequency of about 70 Hz.

9. The apparatus of claim 1, further comprising:
   a sensory indicator that demarcates an approximate range over which said magnetic field is generated.

10. The apparatus of claim 9, wherein said sensory indicator comprises:
   an LED mounted in said housing for illuminating shin over said approximate range of said magnetic field.

11. The apparatus of claim 1, wherein said portable housing comprises a hand-held probe that encloses a single said circuit and straight wire element.

12. The apparatus of claim 1, wherein said housing comprises a conformed pad having a plurality of said circuits and straight wire elements enclosed therein.

13. The apparatus of claim 12, wherein said conformed pad comprises a pliable sheet having said circuits and straight wire elements embedded therein.

14. A method for applying pulsed electromagnetic therapy to humans and animals, said method comprising the steps of:
   positioning a straight wire element in close proximity to an affected area of a body, for generating a magnetic field in response to flow of a current pulse therethrough; and supplying to said straight wire element a current pulse that approximates a square pulse in form, so that said straight wire element generates a magnetic pulse having rapid rise and fall times.

15. The method of claim 14, wherein said magnetic pulse generated by said straight wire element has a sustained peak field strength duration of less than about 500 nanoseconds.

16. The method of claim 15, wherein said magnetic pulse has a duration of about 200 nanoseconds.

17. The method of claim 15, wherein said magnetic pulse has a peak field strength of less than about 5 gauss at a 1 cm distance from said straight wire element.

18. The method of claim 17, wherein said magnetic pulse has a peak field strength of about 2 gauss at a 1 cm distance from said straight wire element.

19. The method of claim 17, wherein said magnetic pulse is repeated with a frequency in the range of about 10–100 Hz.

20. The method of claim 19, wherein said magnetic pulse is repeated with a frequency of about 70 Hz.

* * * * *